United States Patent [19]
Dotan

[11] Patent Number: 5,355,213
[45] Date of Patent: Oct. 11, 1994

[54] INSPECTION SYSTEM FOR DETECTING SURFACE FLAWS

[76] Inventor: Gideon Dotan, 33 Havradim Street, Givat Avia 56 275 Yahud, Israel

[21] Appl. No.: 976,862

[22] Filed: Nov. 16, 1992

[30] Foreign Application Priority Data

Dec. 20, 1991 [IL] Israel .................................. 100443

[51] Int. Cl.$^5$ .......................................... G01N 21/17
[52] U.S. Cl. .................................................. 356/239
[58] Field of Search ....................... 356/237, 239, 73.1

[56] References Cited

U.S. PATENT DOCUMENTS

| | | | |
|---|---|---|---|
| 552,641 | 1/1896 | Hoskins | 356/239 |
| 1,514,386 | 11/1924 | Hitner | 65/158 |
| 3,328,000 | 6/1967 | Rottmann | 250/223 B |
| 3,639,067 | 1/1972 | Stephens | 356/240 |
| 3,985,454 | 10/1976 | Fletcher et al. | 356/239 |
| 4,668,861 | 5/1987 | White | 250/227.21 |
| 4,678,327 | 7/1987 | Yoshida et al. | 356/73.1 |
| 4,808,813 | 2/1989 | Champetier | 356/239 |

Primary Examiner—Richard A. Rosenberger
Attorney, Agent, or Firm—Mark M. Friedman

[57] ABSTRACT

An inspection system for detecting surface flaws in a transparent element which includes a source of electromagnetic radiation, such as a laser beam or visible light, with the radiation beam directed edgewise into the transparent element to be inspected at such an angle that the resulting internal angle is larger than the critical angle. This ensures that substantially all of the radiation will stay within the transparent element and exit through an opposing edge of the transparent element unless a surface flaw is encountered, in which case a portion of the radiation will exit the transparent element through the surface of the transparent element. The system includes a detector, such as a line or matrix charge coupled device, capable of detecting the portion of the radiation which exits the transparent element through the surface of the transparent element and of producing signals corresponding to the exiting radiation.

20 Claims, 6 Drawing Sheets

INSPECTION SYSTEM FOR DETECTING SURFACE FLAWS

FIELD AND BACKGROUND OF THE INVENTION

The present invention relates to an apparatus and a method for detecting surface flaws or contaminants of transparent members, and more particularly, to an apparatus and an automated method using the apparatus for inspecting and detecting, using electromagnetic radiation, the presence of surface flaws and contaminants in the planar or curved surfaces of members which are transparent to the electromagnetic radiation.

Precision components in a great variety of applications require for their proper operation that their surface be essentially free of flaws and contaminants. A significant fraction of such components are made of materials which are transparent to electromagnetic radiation. Examples are the glass substrata used in Liquid Crystal Displays (LCD's) or other Flat Panel Displays (FPD's), windows for Charge Coupled Devices (CCD's) detectors, contact lenses, miniature lenses, glass substrata for rigid disks, etc. For these and similar components, it is imperative that the critical surfaces be virtually free of surface flaws.

In addition, the present invention can also be applied in the inspection of low contrast marks engraved or coated on transparent elements.

Surface flaws can be of a variety of types. The word 'flaw' as used herein is meant to include all types of surface defects such as scratches, digs, pits, chips, and other abnormalities and irregularities which tend to create surface discontinuities. Included also are contaminants which adhere to, or are in contact with, the outer surface of the transparent member, including also contaminants and defects in transparent coatings on the surface.

Since surface flaws are typically very small, it is normally very difficult to detect the defects, specially with high speed automatic systems.

Surface flaw inspection on transparent objects is currently performed largely by visual inspection carried out by human inspectors. The process is labor-intensive and often unreliable.

The inspection process has been automated to some extent. There are currently a number of instruments which can aid in the inspection for surface flaws. For example, systems are known which illuminate the member inspected with a flying spot and which detect the scattered light in the black zone. It is also known to use interferometry principles by detecting interference-patterns created by the interaction of light which passes through the inspected element and a reference light beam.

However these methods suffer from low detectability capabilities, a slow inspection rate which results in low inspection rates, and difficulty in the inspection on non-flat surfaces.

In addition, the existing methods cannot be accurately applied for the inspection of defects in low contrast marks engraved or coated on transparent elements such as in reticles, conductive lines, etc.

There is thus a widely recognized need for an apparatus and a method of inspecting the surface of transparent elements for flaws which can accurately detect the presence of such flaws and which can be used in an automated fashion requiring little or no human judgment.

It would be desirable to have an inspection system for detecting surface flaws which would quickly and reliably determine the presence of surface flaws.

SUMMARY OF THE INVENTION

According to the present invention there is provided an inspection system for detecting surface features, such as flaws, contaminants, or surface marks, in a transparent element, comprising: a source of electromagnetic radiation; directing means for directing the radiation edgewise into the transparent element at such an angle that the angle between the radiation penetrating the element and the surface of the element is larger than the critical angle so that substantially all of the radiation will stay within the transparent element and exit through an opposing edge of the transparent element unless a surface flaw is encountered, in which case a portion of the radiation will exit the transparent element through the surface of the transparent element; a detector capable of detecting the portion of the radiation which exits the transparent element through the surface of the transparent element and of producing signals corresponding to the exiting radiation; and a signal processor capable of processing the signals corresponding to the exiting radiation.

According to the present invention there is also provided a method of inspecting surface features, such as flaws, contaminants or surface marks, in a transparent element, comprising: directing electromagnetic radiation edgewise into the transparent element at an such an angle that the angle between the radiation penetrating the element and the surface of the element is larger than the critical angle so that substantially all of the radiation will stay within the transparent element and exit through an opposing edge of the transparent element unless a surface flaw is encountered, in which case a portion of the radiation will exit the transparent element through the surface of the transparent element; detecting the portion of the radiation which exits the transparent element through the surface of the transparent element and producing signals corresponding to the exiting radiation; and processing the signals corresponding to the exiting radiation.

According to further features in preferred embodiments of the invention described below, there is provided means for moving the transparent element. so as to present different portions of the transparent element for inspection, whether by translation or rotation, or both.

According to an alternative embodiment, the transparent element is kept stationary and the electromagnetic radiation, and, in some cases, the detector, are moved to achieve inspection of the entire transparent element.

A system and method according to the present invention overcomes problems associated with the automatic inspection of defects in transparent elements. Transparent elements having flat or smoothly curved surfaces can be accommodated.

Various types of flaws on the element surface, including coating defects and contamination, can be detected, as can, incidentally, a number of internal defects. Internal defects include bubbles, cracks and other non-surface irregularities which cause non-homogeneity in the material.

Detection of flaws is accomplished by directing radiation edgewise into the element and sensing the radiation which emerges through the element surface. The radiation introduced edgewise into the element is typically a narrow beam, which is introduced in such a way that the radiation enters the transparent element to form an angle between the penetrating radiation and the surface to be inspected which is greater, preferably only slightly greater, than the critical angle.

Introducing the radiation at an angle which is greater than the critical angle ensures that, in the absence of flaws, total internal reflection is achieved and the incident light stays within the transparent element until it reaches the far end of the element where the radiation leaves the element through the far edge of the element.

When a surface flaw exists, some of the radiation will not be internally reflected upon impinging upon the flaw, but will rather escape through the surface of the transparent element. The radiation is preferably directed so that the internal reflecting angle is only slightly larger than the critical angle in order to enhance the sensitivity of the system. When the internal reflection angle is only slightly above the critical, even small imperfections in the surface will cause a portion of the radiation to escape the element, thereby providing an indication of the presence of a flaw. Furthermore, to enhance the light emerging from the element it is preferred to use polarized light.

The scanning can be accomplished in a number of ways, such as by linearly translating or rotating the inspected element. The emerging light is imaged on a line scan camera, which is aligned parallel to the light beam, or on any other suitable detector.

Inspected elements of sufficiently small size may be inspected in their entirety with a single radiation beam without the need to scan the element. In such a case the emerged light may be imaged on a matrix camera (like CCD) or on any other suitable detector.

The signal of the multi-element line detector, or scan camera, or matrix or array camera, or other detector, is processed, for example using a frame grabber and image processor, in order to convert the signals produced by the detector to information useful in identifying the presence, and, when desired, the location, of the flaw. The processor preferably takes advantage of algorithms to optimize the detection and reduce false alarms. Any suitable signal processor may be used. For example threshold signal processing may be applied to determine the signal caused by the flaw.

For inspection of marks on an element, the method and system configuration are virtually identical with those described above for flaw inspection, with differences in the signal processing and interpretation of the results.

Systems and methods according to the present invention have several advantages over currently known inspection methods. In contrast with presently known techniques, the inspection system and method according to the present invention are capable of detecting flaws and contaminants, on one or on both surfaces of the element, as well as in the interior of the inspected element and in its surface coating.

The signal to noise ratio at the detector plane is high, since if no defects are present, almost no light emerges from the element through its surface. This is because, in the absence of flaws, the entire light beam is totally internal reflected within the element. Therefore, the noise is basically the detector noise. The only signal which reaches the detector, is caused by the light exiting the element surface following impingement upon the flaws or contaminants.

The use of an imaging system for detecting the flaws makes it possible to eliminate false alarm, and ensure reliable automatic inspection, through the use of image processing.

A more complete understanding of the present invention, and of its applicability in the inspection, especially automatic inspection, of surface flaws, will be given in the following example and the accompanying drawings.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of an apparatus and a method of inspecting a transparent element for surface flaws. The principles and operation of an apparatus and a method according to the present invention may be better understood with reference to the figures and embodiments described below.

Figure 1:
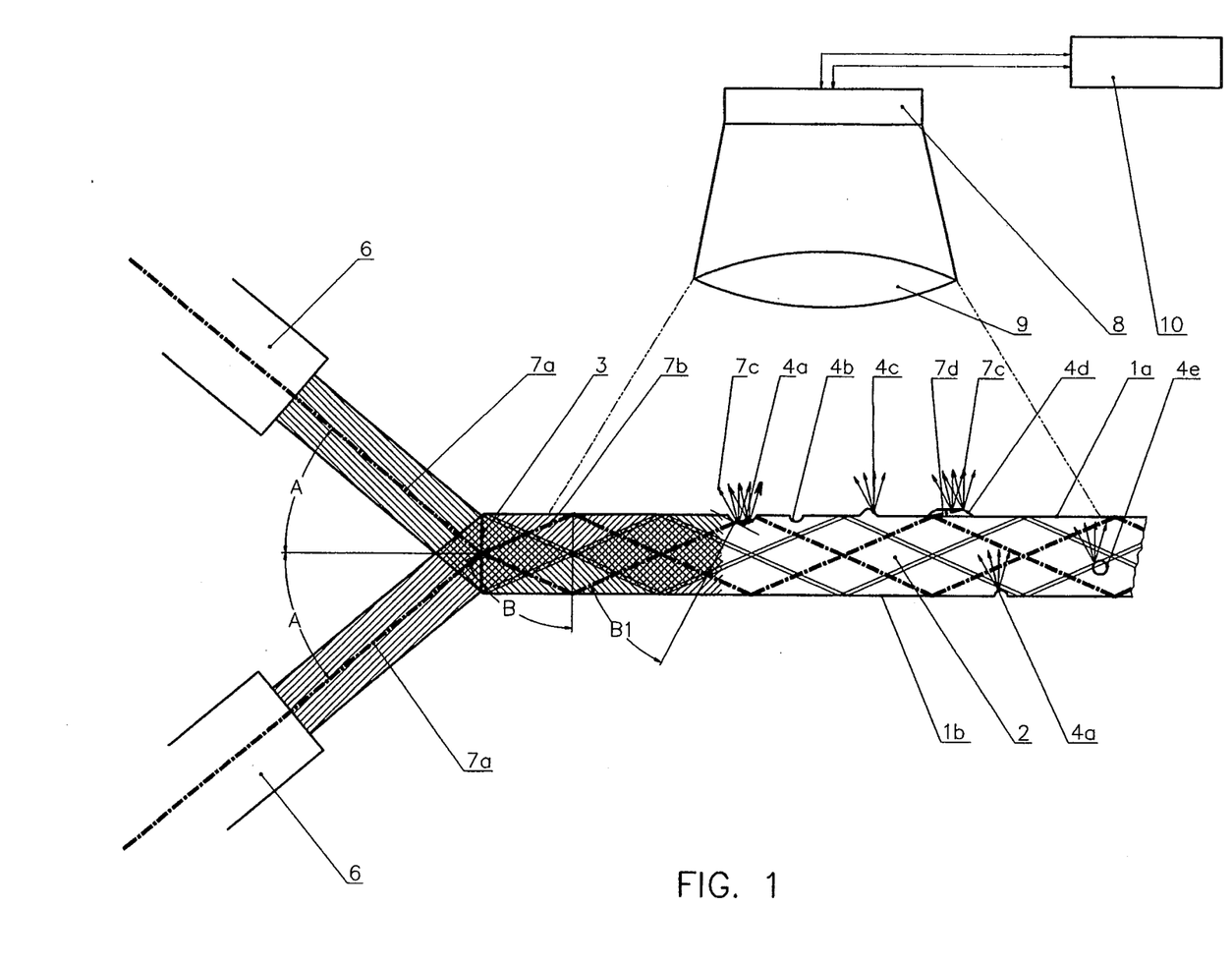
FIG. 1 is a schematic depiction of an inspection method and system according to the present invention.

Referring now to the figures, FIG. 1 depicts an inspection method and system for detecting flaws or contamination on a surface 1a of a transparent element 2. The element is made of a transparent material, and has surfaces 1a and 1b. Surfaces 1a and 1b are depicted as being parallel to each other. While such a configuration is convenient, it is not essential for the operation of a method or a system according to the present invention. Elements with non-parallel surfaces, even with curved surfaces, can also be inspected.

An electromagnetic radiation source 6 illuminates transparent element 2 at one of its edges 3. Any convenient electromagnetic radiation may be used, for example, laser beams. Alternatively, one may use any convenient narrow-band light sources, such as those based on xenon or halogens. Indicated in FIG. 1 are two solid-state lasers. The use of two beams, as depicted in FIG. 1, provides complete coverage of the entire surface to be inspected.

Figure 4:
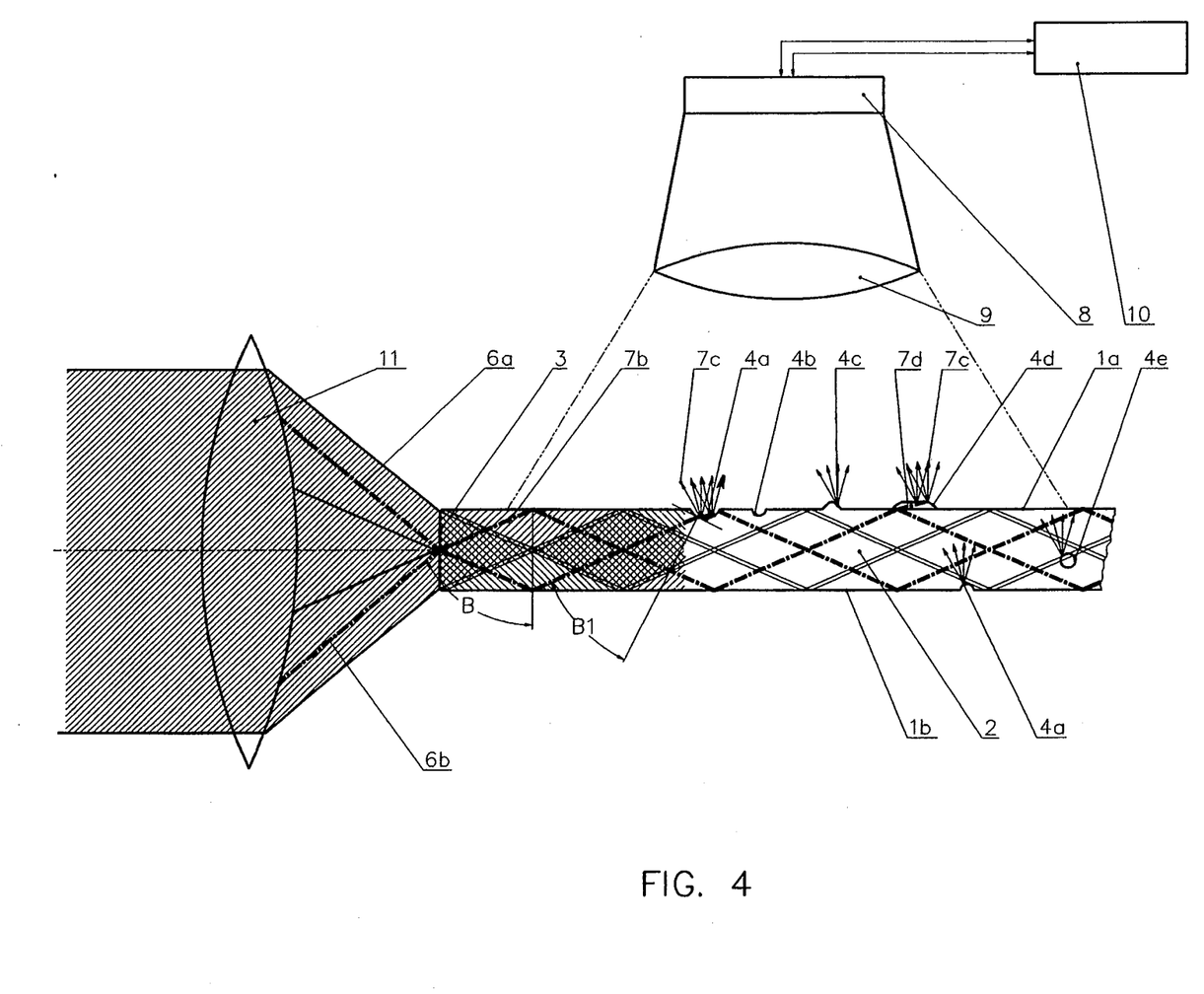
FIG. 4 shows the method and system as in FIG. 1 but using a lens to act on a single radiation beam so as to effectively form a plurality of "beams".

While it is preferably to use two beams, it is not usually necessary to use two separate radiation sources to produce the beams. For example, a single beam may be generated and subsequently split into two beams by optical manipulation. Alternatively, as shown in FIG. 4, it is possible to pass a single beam through a lens 11, preferably a fast lens, or cylindrical lens, which serves to effectively generate two "beams". It may also be possible to use a single beam and vary its position and- /or the position of element 2 to sequentially scan the entire surface to be inspected.

Radiation sources 6 produce radiation beams 7a which are directed in an angle "A", such that the internal rays 7b, which are the rays after their entry into transparent element 2, strike surfaces 1a and 1b at an angle "B" which is slightly greater than the critical angle.

Various directing means may be used to direct the radiation from sources 6 to the object. These include, but are not limited to, direct transmission through the air, and the use of optical light guides. The latter may include fiber optics and may optionally further include a lens or lenses.

Internal rays 7b are totally internally reflected, each time they hit surface 1a or 1b and so propagate through the element. In case internal rays 7b encounter a surface flaw, such as a scratch 4a, a dig 4b, or a pit 4c, the angle "B1" between ray 7b and surface 1a, is less than the critical angle. Therefore the total internal reflection conditions no longer holds, and an escaping ray 7c emerges out of surafce 1a. In case of contaminant 4d is encountered, ray 7d penetrates the contaminant, and, once again, the condition of total internal reflectance is violated and the ray emerges from contaminant 4d.

Radiation leaving surface 1a is focused on a line scan CCD 8, by a lens 9. Line CCD 8 senses the emitted light and transmits a signal to a signal processor 10. If no surface flaws or contaminants are encountered, almost no light leaves through surface 1a, and so no radiation reaches line CCD 8.

To achieve the inspection of the while inspected surface, transparent element 2 is moved perpendicularly to the radiation beam 7a, so the whole area of the element is scanned. The movement is carried out in such a way as to ensure that radiation beam 7a always enters element 2 through its edge 3. Alternatively, element 2 may be held steady while radiation beam 7b, and possibly other portion of the system, are moved. In yet another possibility, both element 2 and radiation beam 7b may be moved in some coordinated fashion to achieve the objective of subjecting the entire surface of element 2 for inspection.

Figure 2A:
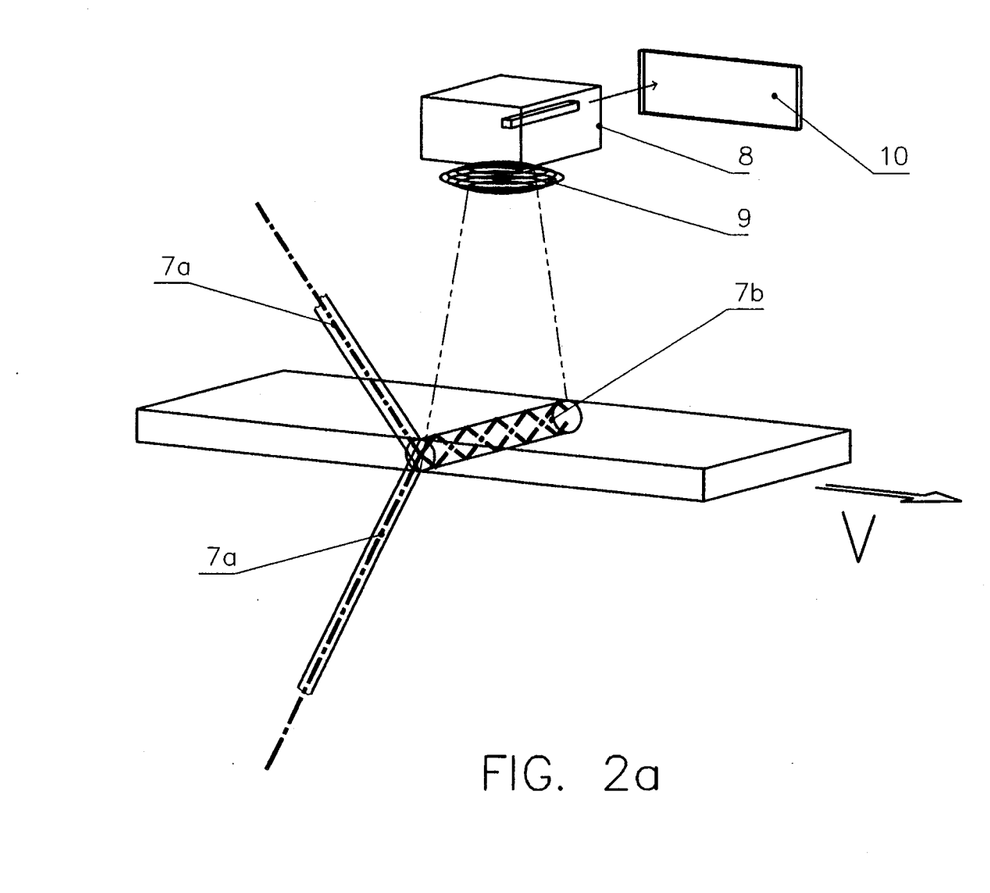
FIG. 2a shows the system of FIG. 1 where the inspected element can be translated linearly.
Figure 2B:
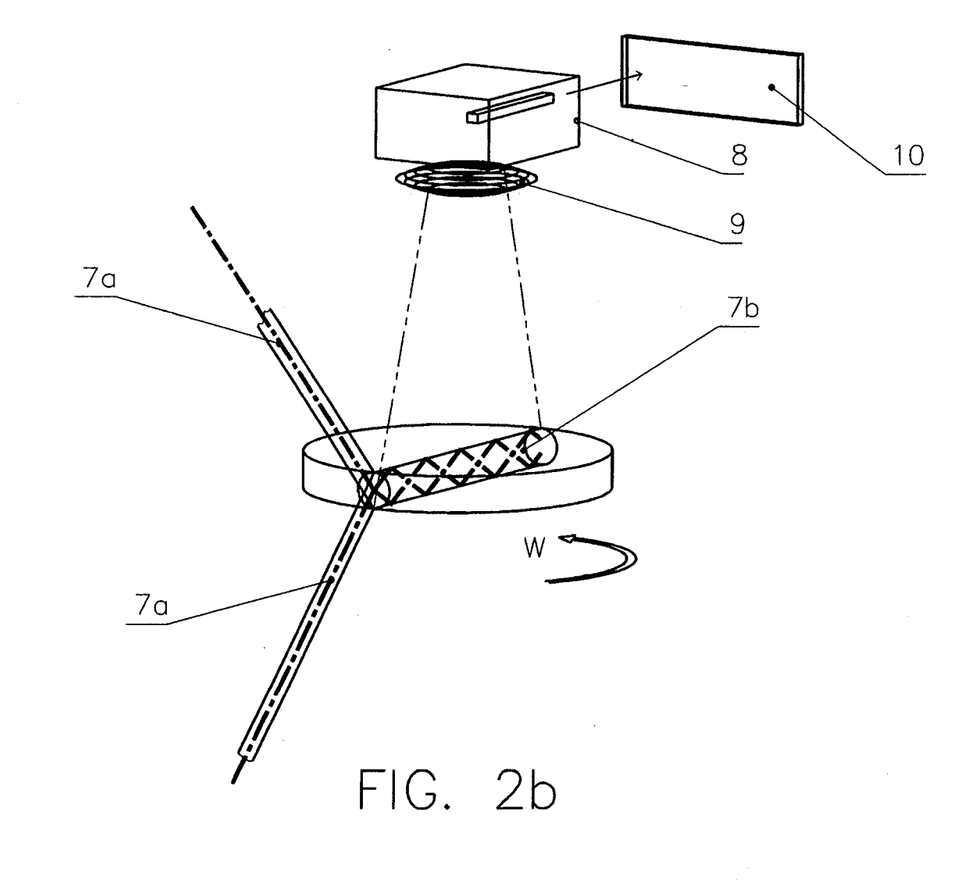
FIG. 2b shows the system of FIG. 1 where the inspected element can be rotated about a vertical.
Figure 2C:
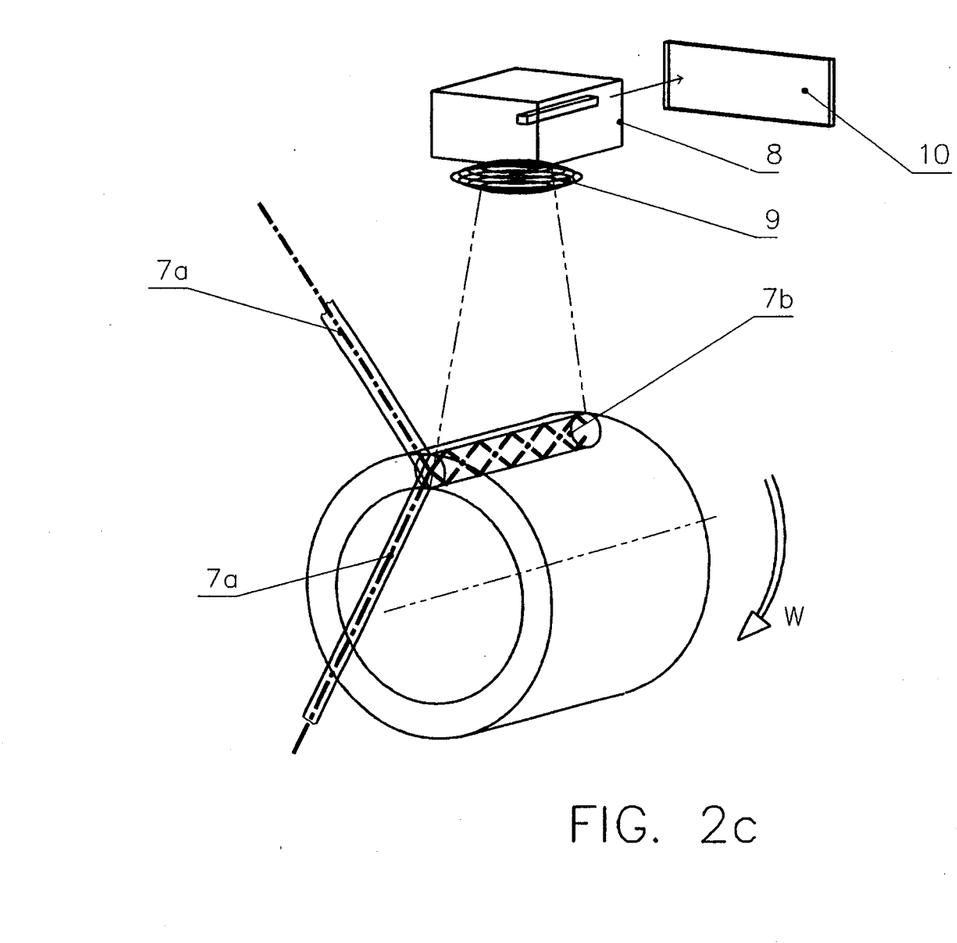
FIG. 2c shows the system of FIG. 1 where the inspected element can be rotated about its axis.

Each of these modes of scanning is consistent with FIGS. 1 and 4. If the element has a substantially rectangular edge 3, element 2 can be moved linearly in direction "V" as shown in FIG. 2a. If the element is substantially disk-shaped, it can be rotated about its axis, as shown in FIG. 2b. If the element is substantially a hollow cylinder, radiation beam 7a is directed to the cylinder base, and the cylinder can be rotated about its axis, as shown in FIG. 2c. Alternatively, element 2 can be held in a fixed position and radiation beam 7a and, if necessary, CCD 8 (which may include electronic components, making it a camera), can be moved so as to scan the surface of element 2 for flaws and contaminants.

The signal produced by line scan camera 8 is processed by an image processor 10 in order to detect and identify the signals from the flaw or contamination, and so to eliminate false alarms.

Figure 3:
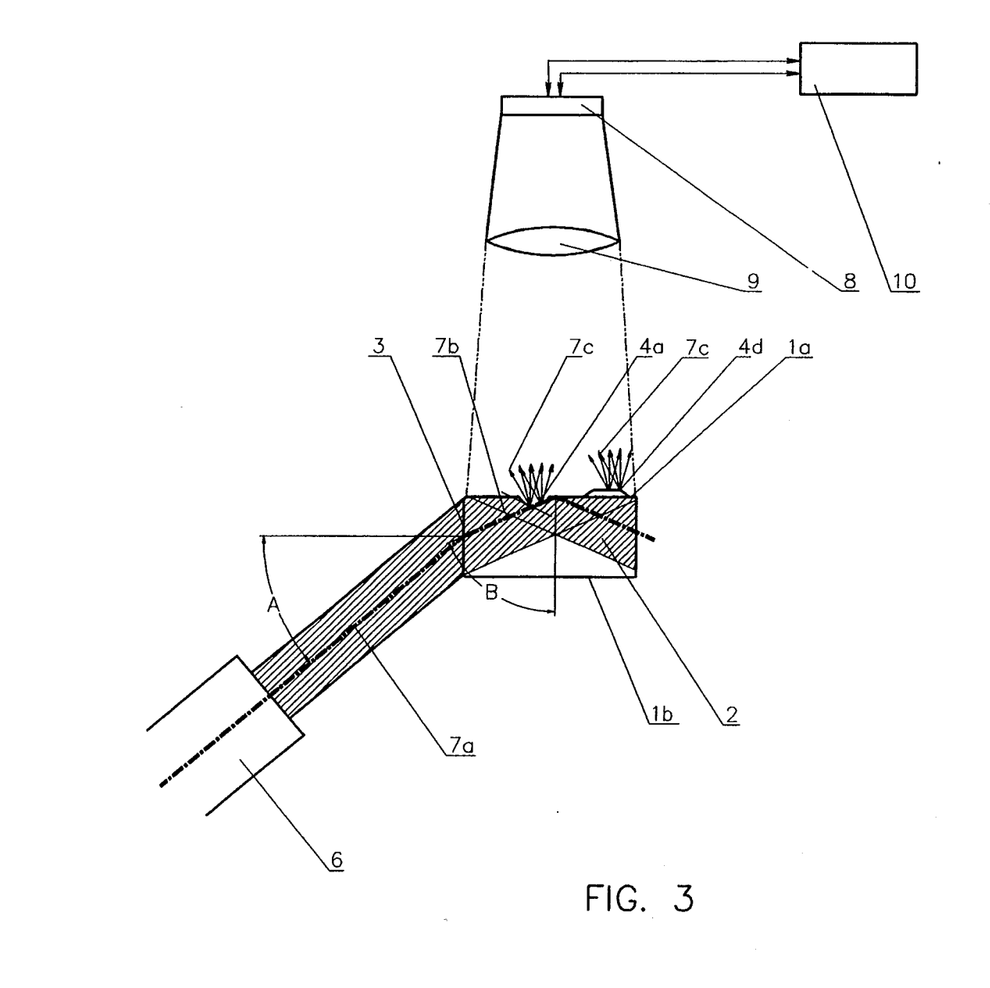
FIG. 3 shows a system according to the present invention wherein a single beam is able to illuminate the entire inspected surface of the element without the need to move either the beam or the element.

If element 2 is relatively small, surface 1a in its entirely can be illuminated with beam 7b as illustrated in FIG. 3. In this case no scanning is needed. Instead of using line CCD 8, a matrix CCD 8 is used, and surface 1a is focused on it by lens 9. The signal of CCD 8 (which may include electronic components, making it a camera), is processed by image processor 10 in order to identify the flaw and eliminate false alarms.

While the invention has been described with respect to one preferred embodiment, it will be appreciated that many variations, modifications and other applications of the invention may be made.

What is claimed is:

1. An inspection system for detecting surface features, such as flaws, contaminants, and surface marks, in a transparent element, comprising:
   (a) a collimated beam of electromagnetic radiation;
   (b) directing means for directing said collimated beam edgewise into the transparent element at such an angle that the angle between said collimated beam penetrating the element and the surface of the element is larger than the critical angle so that substantially all of said radiation will stay within said transparent element and exit through an opposing edge of the transparent element unless a surface flaw is encountered, in which case a portion of said radiation will exit the transparent element through the surface of the transparent element;
   (c) a multi-element line detector capable of detecting said portion of sad radiation which exits the transparent element through the surface of the transparent element and of producing signals corresponding to said exiting radiation;
   (d) a signal processor capable of processing said signals corresponding to said exiting radiation; and
   (e) means for creating relative motion between the transparent element and said beam.

2. A system as in claim 1, wherein said means for creating relative motion includes moving the transparent element so as to present different portions of the transparent element for inspection.

3. A system as in claim 2, wherein said directing means includes optical light guides.

4. A system as in claim 1, wherein said means for creating relative motion includes moving said radiation in such a way that different portions of the transparent element are inspected.

5. A system as in claim I wherein said electromagnetic radiation is a laser beam, a xenon beam or a halogen beam.

6. A system as in claim 1, wherein said radiation includes a plurality of beams.

7. A system as in claim I further including a lens which serves to create a plurality of beams.

8. A system as in claim I wherein said detector is a multi-element line detector or an array detector.

9. A system as in claim I wherein the surface feature to be inspected is a defect in an intentionally created surface mark.

10. A method of inspecting surface features, such as flaws, contaminants, or surface marks, in a transparent element, comprising:
   (a) directing a collimated electromagnetic radiation beam edgewise into the transparent element at such an angle that the resulting internal angle is larger than the critical angle so that substantially all of said radiation will stay within said transparent element and exit through an opposing edge of the transparent element unless a surface flaw is encountered, in which case a portion of said radiation will exit the transparent element through the surface of the transparent element;

(b) creating relative motion between the transparent element and said beam;

(c) detecting said portion of said radiation which exits the transparent element through the surface of the transparent element using a multi-element line detector and producing signals corresponding to said exiting radiation; and (d) processing said signals corresponding to said exiting radiation.

11. A method as in claim 10, wherein said creating relative motion includes moving the transparent element so as to present different portions of the transparent element for inspection.

12. A method as in claim 11, wherein said moving includes translating the transparent element.

13. A method as in claim 11, wherein said moving includes rotating the transparent element.

14. A system as in claim 11, wherein said directing means includes optical light guides.

15. A method as in claim 10, wherein said directing includes moving said radiation in such a way that different portions of the transparent element are inspected.

16. A method as in claim 10 wherein said electromagnetic radiation is a laser beam, a xenon beam or a halogen beam.

17. A method as in claim 10, wherein said radiation includes a plurality of beams.

18. A method as in claim 10 further including a lens which serves to create a plurality of beams.

19. A method as in claim 10 wherein said detecting is accomplished using a multi-element line detector or an array detector.

20. A method as in claim 10 wherein the surface feature to be inspected is a defect in an intentionally created surface mark.

* * * * *